United States Patent [19]

D'Amico

[11] 3,992,185

[45] Nov. 16, 1976

[54] DITHIO AND THIOL CARBAMATES AS PLANT GROWTH REGULANTS

[75] Inventor: John J. D'Amico, Olivette, Mo.

[73] Assignee: Monsanto Company, St. Louis, Mo.

[22] Filed: Mar. 19, 1975

[21] Appl. No.: 559,843

[52] U.S. Cl. .................................... 71/76; 71/72; 71/100; 71/101
[51] Int. Cl.$^2$ ............................................. A01N 9/12
[58] Field of Search .................... 71/100, 101, 76

[56] References Cited
UNITED STATES PATENTS

| | | | |
|---|---|---|---|
| 2,992,091 | 7/1961 | Harman et al. .................... | 71/100 |
| 3,647,850 | 3/1972 | Ono et al. ........................ | 71/101 X |
| 3,687,653 | 8/1972 | Bollinger et al. ................. | 71/100 X |
| 3,715,199 | 2/1973 | Wakamorl et al. ................ | 71/101 |
| 3,732,272 | 5/1973 | Tilles ............................... | 71/100 X |

FOREIGN PATENTS OR APPLICATIONS 1,301,032   12/1972   United Kingdom .................. 71/101

*Primary Examiner*—Lewis Gotts
*Assistant Examiner*—Catherine L. Mills
*Attorney, Agent, or Firm*—Richard H. Shear; Donald W. Peterson

[57] ABSTRACT

The regulation of plant growth is achieved through the use of substituted dithio and thiol carbamates.

9 Claims, No Drawings

DITHIO AND THIOL CARBAMATES AS PLANT GROWTH REGULANTS

The present invention relates to a method of regulating the growth of leguminous plants, particularly soybean. More specifically, this invention relates to the use of dithio and thiol carbamates as the active ingredient in compositions useful to regulate plant growth.

The class of dithio and thiol carbamates useful in accordance with this invention may be characterized by the formula

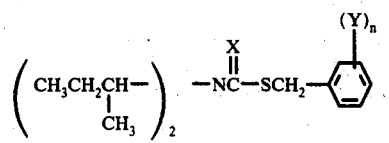

wherein X may be S or O, and Y may be F or when X is O, Y may be Cl in the 4 position, and $n$ is 0 or 1.

Representative compounds of the above formula preferred in accordance with this invention include:

I Benzyl N,N-di-sec-butyldithiocarbamate
II 2-Fluorobenzyl N,N-di-sec-butyldithiocarbamate
III Benzyl N,N-di-sec-butyldithiocarbamate
IV 4-Chlorobenzyl N,N-di-sec-butylthiolcarbamate
V 4-Fluorobenzyl N,N-di-sec-butyldithiocarbamate The term "plant regulant", as employed in this application, connotes a material which serves to modify the normal sequential development of a treated plant to agricultural maturity. Such modification may result from the effect of the material on the physiological processes of the plant or from the effect of said material on the morphology of the plant. It should additionally be recognized that modifications may also result from a combination or sequence of both physiological and morphological factors.

Modifying effects of a plant regulant are probably most readily observed as changes in the size, shape, color or texture of the treated plant or any of its parts. Similarly, changes in the quantity of the plant fruit or flowers are also quite apparent from simple, visual inspection. The above changes may be characterized as an acceleration or retardation of plant growth, stature reduction, leaf or canopy alteration, increased branching, tillering, terminal inhibition, increased flowering or fruit set, increased root growth, stool or sprout inhibition, delayed budding, defoliation, desiccation, delayed senescence, prolongated dormancy, increased cold hardiness, delayed or accelerated ripening, thinning of fruit, prevention of pre-harvest fruit drop, loosening of fruit and the like.

Modifications in the normal sequential development of a treated plant to agricultural maturity may also be manifested by reduced transpiration or increased carbohydrate deposition or protein content.

Although many of the above modifications are per se desirable, it is most often the ultimate effect of such modifications on the economic factor that is of primary significance. For example, reducing the physical size of each plant in a field permits the growing of more plants per unit area and leads to more efficient use of cropland. Many plants of reduced stature are more tolerant of drought and cold temperatures and are more resistant to pest infestations and to lodging. Further, a reduction in the maturation rate on portions of a crop permits an extended harvest period at peak yield and more efficient use of subsequent crop processing equipment.

Some of the compounds of the formula heretofore described are known to possess herbicidal activity. The herbicidal use of such compounds is not within the scope of the present invention. Thus, the regulation of plants in accordance with the instant invention does not include the total inhibition or the killing of such plants. Although phytotoxic amounts of the materials disclosed herein might be employed to exert a herbicidal (killing) action, it is contemplated here to employ only plant regulating amounts of such materials in order to modify the normal sequential development of the treated plant to agricultural maturity. The application of a plant regulating amount may be made to plants in sequence at various stages of the plants' development to obtain various desirable responses. As may be expected, and as is apparent to those skilled in the art, such plant regulating amounts will vary, not only with the material selected, but also with the modifying effect desired, the species of plant and its stage of development, the plant growth medium and whether a permanent or transitory effect is sought.

In accordance with this invention it has been found that desirable modification of plants is achieved by applying the above-described plant regulants to seeds, emerging seedlings, roots, stems, leaves, flowers, fruits or other plant parts. Such application may be made directly to the plant part, or indirectly by application to the plant growing medium.

The term "active ingredient" is used herein to describe the dithio and thiol carbamates of the foregoing formula. In practicing the plant growth regulating methods of this invention, the active ingredients can be used alone or in combination with a material referred to in the art as an adjuvant in liquid or solid form. The plant growth regulating compositions of this invention are prepared by admixing the active ingredient with an adjuvant including diluents, extenders, carriers and conditioning agents to provide compositions in the form of finely-divided particulate solids, granules, pellets, wettable powders, dusts, solutions and aqueous dispersions or emulsions. Thus, the active ingredient can be used with an adjuvant such as a finely divided particulate solid, a solvent liquid of organic origin, water, a wetting agent, dispersing agent, or emulsifying agent or any suitable combination of these.

Illustrative finely divided solid carriers and extenders which are useful in the plant growth regulating compositions of this invention, include, for example, the talcs, clays, pumice, silica, diatomaceous earth, quartz, Fullers earth, sulfur, powdered cork, powdered wood, walnut flour, chalk, tobacco dust, charcoal and the like. Typical liquid diluents include, for example, Stoddard solvent, acetone, alcohols, glycols, ethyl acetate, benzene and the like. The plant growth regulating compositions of this invention, particularly liquids and wettable powders, usually contain as a conditioning agent one or more surface-active agents in amounts sufficient to render a given composition readily dispersible in water or in oil. By the term "surface active agent" it is understood that wetting agents, dispersing agents, suspending agents and emulsifying agents are included therein. Anionic, cationic, and non-ionic agents can be used with equal facility.

Preferred wetting agents are alkyl benzene and alkyl naphthalene sulfonates, sulfated fatty alcohols, amines or acid amides, long chain acid esters of sodium isothionate, esters of sodium sulfosuccinate, sulfated or sulfonated fatty acid esters petroleum sulfonates, sulfonated vegetable oils, ditertiary acetylenic glycols, polyoxyethylene derivatives of alkylphenols (particularly isooctylphenol and nonylphenol) and polyoxyethylene derivatives of the mono-higher fatty acid esters of hexitol anhydrides (e.g. sorbitan). Preferred dispersants are methyl cellulose, polyvinyl alcohol, sodium lignin sulfonates, polymeric alkyl naphthalene sulfonates, sodium naphthalene sulfonate, polymethylene bisnaphthalenesulfonate and sodium N-methyl-N-(long chain acid) laurates.

Water-dispersible powder compositions can be made containing one or more active ingredients, an inert solid extender and one or more wetting and dispersing agents. The inert solid extenders are usually of mineral origin such as the natural clays, diatomaceous earth and synthetic minerals derived from silica and the like. Examples of such extenders include kaolinites, attapulgite clay and synthetic magnesium silicate. The water-dispersible powder of this invention usually contain from about 5 to about 95 parts by weight of active ingredient, from about 0.25 to 25 parts by weight of wetting agent, from about 0.25 to 25 parts by weight of dispersant and from 4.5 to about 94.5 parts by weight of inert solid extender, all parts being by weight of the total composition. Where required, from about 0.1 to 2.0 parts by weight of the solid inert extender can be enhanced by a corrosion inhibitor or anti-foaming agent.

Aqueous suspensions can be prepared by mixing together and grinding an aqueous slurry of water-insoluble active ingredient in the presence of dispersing agents to obtain a concentrated slurry of very finely-divided particles. The resulting concentrated aqueous suspension is characterized by its extremely small particle size, so that when diluted and sprayed, coverage is very uniform.

Emulsifiable oils are usually solutions of active ingredient in water-immiscible or partially water-immiscible solvents together with a surface active agent. Suitable solvents for the active ingredient of this invention include hydrocarbons and water-immiscible ethers, esters or ketones. The emulsifiable oil compositions generally contain from about 5 to 95 parts active ingredients, about 1 to 50 parts surface active agent and about 4 to 94 parts solvent, all parts being by weight based on the total weight of emulsifiable oil.

Generally, the active ingredients are applied in the form of a composition containing one or more of the above described adjuvants which aid in the application of a uniform distribution of the active ingredient. The application of liquid and particulate solid compositions of the active ingredient can be carried out by conventional techniques, utilizing, for example, spreaders, power dusters, boom and hand sprayers and spray dusters. The compositions can also be applied from airplanes as a dust or spray. The application of the plant growth regulating compositions to the plant growth medium is generally carried out by incorporating the compositions in the soil or other media in the area where modification of the plants is desired.

In selecting the appropriate non-toxic rate of application of the active ingredient it will be recognized that precise rates will also be dependent upon the mode of application, such as soil incorporation, band application, pre-plant seed treatment and various other factors known to those skilled in the art. In foliar treatments for the regulation of plant growth, the active ingredients are applied in amounts from about 0.05 to about 10 or more pounds per acre. Foliar applications of from 0.1 to 5 pounds of the active ingredient per acre are preferred. In applications to the soil habitat of germinant seeds, emerging seedlings, and established vegetation for the regulation of plant growth, the active ingredients are applied in amounts of from about 0.01 to about 20 pounds per acre or more. Preferably, the active ingredients are applied to the soil at a rate of from 0.1 to 10 pounds per acre. Foliar application to plants beginning to blossom are particularly advantageous and are preferred.

In accordance with the present invention, certain dithio and thiol carbamates are found to be effective growth regulators for leguminous plants, as represented by soybean (Glycine max). Differences between those legumes treated with the active ingredient and those not treated are a reduction in stature, leaf inhibition and early pod set. Other differences are noted as well. By reducing the stature of the plant and inhibiting vegetative growth, the growing energy utilized by the plant is directed more toward fruiting and less toward vegetative growth. This causes an increase in the plant's efficiency of production as well as an increase in the number of plants per unit area providing for an optimization of crop output. Further, shorter plants undergo less lodging. Thus, when harvested, less plants are lost and the yield can be increased.

In accordance with the practice of the invention, several plant growth regulating compositions were formulated utilizing various dithio and thiol carbamates as the active ingredient. The most preferred active ingredient is benzyl di-sec-butyldithiocarbamate. The compositions were formulated so that they could be applied at a rate the equivalent of 200 gallons per acre (1892 liters per hectare). Table I illustrates the formulation for several application rates of active ingredient. In each formulation, the stock solution utilized is 1% of the active ingredient dissolved in acetone.

TABLE I

| RATE Lbs/Acre (kilos/hectare) | ml. of 1% Stock Solution | ml. Acetone | ml. 0.39% TWEEN 20 In Water As Surfactant |
|---|---|---|---|
| 6.0 (6.72) | 2.0 | — | 3.6 |
| 5.0 (5.60) | 2.0 | 1.0 | 3.7 |
| 3.0 (3.36) | 1.0 | 1.0 | 3.6 |
| 2.5 (2.80) | 1.0 | 2.0 | 3.7 |
| 1.2 (1.34) | 0.4 | 1.6 | 3.6 |
| 1.0 (1.12) | 0.4 | 2.6 | 3.7 |
| 0.6 (.672) | 0.2 | 1.8 | 3.6 |
| 0.5 (.560) | 0.2 | 2.8 | 3.7 |
| 0.3 (.336) | 0.1 | 1.9 | 3.6 |

Utilizing compositions formulated in accordance with TABLE I, several dithio and thiol carbamates exhibited unexpected plant growth regulatory properties as illustrated by the test set forth in Example 1.

EXAMPLE 1

A number of soybean plants, variety Corsoy, are grown from seeds in aluminum pans in the greenhouse for a period of approximately one week to the primary leaf stage. The plants are thinned to three uniform plants in each pan and the height of each plant in the pan is measured to the terminal bud and the average height is noted. One pan containing three soybean plants is used for each chemical treatment and three pans are not treated and used as a control. The composition as formulated in accordance with TABLE I is then applied to the pan of growing plants by overhead spray at a rate equivalent to the desired rate of active ingredient per acre. The treated pans, along with the control pans, are maintained in a greenhouse and watered from below on a sand bench and fertilized with a uniform portion of a water-soluble balanced fertilizer.

Two weeks after application of the chemical, the average height of the soybean plants in the treated pan is again measured as above and the difference in the average height before and two weeks after application represent the increase in the development of the treated pans. This development in growth of the treated plants is compared to the average increase in growth of the plants in the control pans during the same period of time. A variation of 25% or more in the development of at least two-thirds of the treated plants when compared to the development of the control plants demonstrates that the chemical in an effective plant regulant. Thus, a chemical is considered active when treated plants manifest a decrease in growth of at least 25% less than that of the control plants, i.e., stature reduction, or an increase in growth in excess of 25% of that of the control plants, i.e., growth stimulation.

Table II below summarizes the results and observations made in accordance with Example 1 when the dithio and thiol carbamates of the invention were utilized as the active ingredient at several rates.

TABLE II

| Compound | RATE Lb/Acre (kilos/hectare) | | Result |
|---|---|---|---|
| I | 6.0 | (6.72) | Stature Reduction, Axillary Bud Development, Leaf Distortion |
| | 3.0 | (3.36) | Stature Reduction, Axillary Bud Development, Leaf Distortion, Leaf Inhibition |
| | 1.2 | (1.34) | Axillary Bud Development, Leaf Distortion, Leaf Inhibition |
| II | 6.0 | (6.72) | Stature Reduction, Axillary Bud Development, Leaf Distortion, Leaf Inhibition, Inhibition of Apical Development, Slight Leaf Burn |
| | 3.0 | (3.36) | Stature Reduction, Axillary Bud Development, Leaf Distortion, Leaf Inhibition, Inhibition of Apical Development, Slight Leaf Burn |
| | 1.2 | (1.34) | Stature Reduction, Leaf Distortion, Leaf Inhibition, Axillary Bud Development, Inhibition of Apical Development |
| | 0.6 | (0.672) | Stature Reduction, Leaf Distortion, Leaf Inhibition, Axillary Bud Development, Inhibition of Apical Development, Slight Leaf Burn |
| | 0.3 | (0.336) | Leaf Distortion, Leaf Inhibition, Slight Leaf Burn |
| III | 6.0 | (6.72) | Stature Reduction, Inhibition of Apical Development, Axillary Bud Development, Leaf Inhibition |
| | 1.8 | (2.016) | Stature Reduction, Leaf Distortion, Leaf Inhibition |
| IV | 6.0 | (6.72) | Leaf Distortion, Leaf Inhibition, Slight Leaf Burn |
| | 3.0 | (3.36) | Stature Reduction, Leaf Distortion, Inhibition of Apical Development |
| | 1.2 | (1.34) | Leaf Distortion |
| V | 6.0 | (6.72) | Stature Reduction, Axillary Bud Development, Leaf Distortion, Leaf Inhibition |
| | 3.0 | (3.36) | Stature Reduction, Axillary Bud Development, Leaf Distortion, Leaf Inhibition |
| | 1.2 | (1.34) | Stature Reduction, Axillary Bud Development, Leaf Distortion |

Further advantages of this invention are shown in Example 2.

EXAMPLE 2

Individual soybean plants, variety Corsoy, are grown from seed in 6 inch pots containing a good grade of top soil. Two pots of 6-week old plants (5–6 trifoliate stage) are used for each application of the chemical. An overhead spray of an aqueous composition of the chemical is applied to the pots at an equivalent rate as indicated below. Two to four sets of plants which received no chemical application are included and serve as controls. All of the pots are maintained under good growing conditions and are watered and are fertilized with a uniform amount of a water-soluble balanced fertilizer. Two weeks after the application of the chemical, the growth responses of the treated plants are compared with that of the control plants. The total height of the plant is measured to the tip of the terminal bud. A variation of 15% in the average total height of the treated plants, when compared to the average total height of the control plants, demonstrate that the chemical is an effective plant growth regulator. Observations made utilizing the test procedure of Example 2 are summarized in TABLE III.

TABLE III

| Compound | RATE Lb/Acre (Kilos/Hectare) | | Result |
|---|---|---|---|
| I | 5.0 | (5.60) | Stature Reduction, Defoliation, Leaf Inhibition, Selective Apical Kill, Early Pod Set, Axillary Bud Inhibition, Slight Leaf Burn |
| | 2.5 | (2.80) | Axillary Bud Development, Leaf Distortion, Early Pod Set, Enhanced Pod Set, Slight Leaf Burn |
| II | 2.5 | (2.80) | Stature Reduction, Defoliation, Leaf Inhibition, Selective Apical Kill, Axillary Bud Inhibition, Slight Leaf Burn |
| | 1.0 | (1.12) | Leaf Distortion, Axillary Bud Inhibition, Slight Leaf Burn |
| III | 2.5 | (2.80) | Stature Reduction, Leaf |

TABLE III-continued

| Compound | RATE Lb/Acre (Kilos/ Hectare) | | Result |
|---|---|---|---|
| | 1.0 | (1.12) | Distortion, Inhibited Pod Set Stature Reduction, Leaf Distortion, Delayed Pod Set, Inhibited Pod Set |
| | 0.5 | (0.560) | Stature Reduction, Leaf Distortion |
| IV | 2.5 | (2.80) | Stature Reduction, Leaf Distortion |
| | 1.0 | (1.12) | Leaf Distortion, Delayed Pod Set, Inhibited Pod Set |
| | 0.5 | (0.560) | Leaf Distortion, Delayed Pod Set, Inhibited Pod Set |
| V | 2.5 | (2.80) | Stature Reduction, Leaf Distortion, Inhibition of Apical Development, Delayed Pod Set, Inhibited Pod Set, Slight Leaf Burn |
| | 1.0 | (1.12) | Stature Reduction, Leaf Distortion, Leaf Inhibition, Slight Leaf Burn |
| | 0.5 | (0.560) | Leaf Distortion, Slight Leaf Burn |

Generally, the thiol carbamates of the invention are prepared by adding the particular substituted or unsubstituted benzyl chloride to a solution comprising di-sec-butylamine, aqueous sodium hydroxide and water to which carbonyl sulfide has been previously added.

In order to more fully illustrate the preparation, the following examples are presented.

EXAMPLE 3

Preparation of Compound III

To a solution comprising 54.3 g. (0.42 moles) of di-sec-butylamine, 24 g. (0.3 moles) of 50% aqueous sodium hydroxide, and 100 ml. of water at 0° – 10° C. is added 23.3 g. (0.33 moles) of 85% carbonyl sulfide in 30 minutes. Benzyl chloride (0.3 moles) is then added in one portion and the reaction mixture is stirred at a temperature of 0° – 5° C. for the first hour, 5° – 10° C. for the second hour, 10° – 15° C. for the third hour, 15° – 20° C. for the fourth hour, 20° – 25° C. for the fifth hour and at 25° – 30° C. for the next 18 hours. 200 ml. of water and 500 ml. of ethyl ether is then added to the stirred reaction mixture and the stirring is continued for 15 minutes. The separated ether layer is then washed with water until neutral and dried over sodium sulfate. The ether is removed under vacuum at a maximum temperature of 80° – 90° C. at 1 – 2 mm. The products are distilled and collected under vacuum.

EXAMPLE 4

Preparation of Compound IV

The procedure of Example 3 is repeated utilizing p-chlorobenzyl chloride in lieu of benzylchloride.

EXAMPLE 5

Preparation of Compound V

The procedure of Example 3 is repeated utilizing p-fluorobenzylchloride in lieu of benzylchloride.

Table IV illustrates the data obtained when the compounds useful in accordance with the invention were prepared utilizing the synthesis of Examples 3 – 5.

TABLE IV

| Compound | State | $N_D^{25}$ | bp °C | % Yield |
|---|---|---|---|---|
| III | Colorless Liquid | 1.5393 | 144/0.8 mm | 56 |
| IV | Colorless Liquid | 1.5458 | 154–5/0.05 mm | 56 |
| V | Colorless Liquid | 1.5253 | 138–40/0.01 mm | 52 |

| | %N | | %S | | %C | | %H | | %Cl | | %F | |
|---|---|---|---|---|---|---|---|---|---|---|---|---|
| Compound | Calc'd. | Found | Calc'd. | Found | Calc'd. | Found | Calc'd. | Found | Calc'd. | Found | Calc'd. | Found |
| III | 5.01 | 4.97 | 11.47 | 11.33 | 68.76 | 68.98 | 9.01 | 8.93 | | | | |
| IV | 4.46 | 4.30 | 10.21 | 10.31 | | | | | 11.29 | 11.48 | | |
| V | 4.70 | 4.57 | 10.78 | 10.61 | | | | | | | 6.38 | 6.70 |

NMR spectra were in agreement with the structures.

The dithio carbamates are prepared by adding carbon disulfide and the particular substituted or unsubstituted benzyl chloride to a solution of di-sec-butylamine, dimethylformamide and aqueous sodium hydroxide.

To more fully illustrate the preparation of the dithio carbamates, the following examples are presented.

EXAMPLE 6

Preparation of Compound I

Carbon disulfide (0.3 moles) is added dropwise at a temperature of 0° – 10° C. to a stirred solution of 38.8 g. (0.3 moles) of di-sec-butylamine, 150 ml. of dimethylformamide and 24 g. (0.3 moles) of 50% aqueous sodium hydroxide. After stirring for one hour at 25° –30° C., 0.25 moles of benzyl chloride is added in one portion. An exothermic reaction sets in causing a temperature rise of about 30° C. The reaction mixture is then stirred at 25°–30° C. for about two days. After the addition of 500 ml. of water and 600 ml. of ethyl ether, stirring is continued for 15 minutes. The separated ether layer is washed with water until neutral and dried over sodium sulfate. The ether is removed in vacuo at a maximum temperature of 80° – 90° C. at 1 – 2 mm.

EXAMPLE 7

Preparation of Compound II

The procedure of Example 6 is followed utilizing o-fluorobenzyl chloride in lieu of benzyl chloride.

Dithio carbamates of the formula

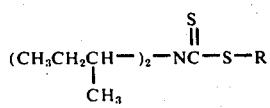

prepared in accordance with the above examples yielded data illustrated by Table V.

TABLE V

| R | State | $N_D^{25}$ | % Yield | %N Calc'd. | %N Found | %S Calc'd. | %S Found |
|---|---|---|---|---|---|---|---|
| —CH₂—C₆H₅ | Amber Liquid | 1.5915 | 95 | 4.74 | 4.88 | 21.70 | 21.87 |
| —CH₂—C₆H₄—F (4-F) | Amber Liquid | 1.5782 | 99 | 4.47 | 4.47 | 20.46 | 20.69 |
| —CH₂—C₆H₄—F | Amber Liquid | 1.5762 | 98 | 4.47 | 4.56 | 20.46 | 20.63 |
| —CH₂—C₆H₄—F (2-F) | Amber Liquid | 1.5774 | 78 | 4.47 | 4.60 | 20.46 | 20.63 |

NMR spectra were in agreement with the structures.

Although this invention has been described with respect to specific modifications, the details thereof are not to be construed as limitations, for it will be apparent that various equivalents, changes and modifications may be resorted to without departing from the spirit and scope thereof and it is understood that such equivalent embodiments are intended to be included herein.

What is claimed is:

1. A method of reducing the stature of leguminous plants comprising treating said plants with an effective, non-lethal plant growth regulating amount of a compound of the formula

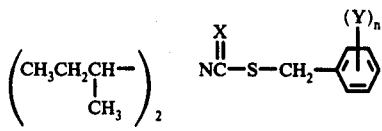

wherein X is S or O; Y is F, or Cl in the 4 position when X is O; and $n$ is 0 or 1.

2. A method in accordance with claim 1 wherein X is S or O, and $n$ is O.

3. A method in accordance with claim 1 wherein X is S.

4. A method in accordance with claim 1 wherein said compound is benzyl, N,N-di-sec-butyldithiocarbamate.

5. A method in accordance with claim 1 wherein said compound is 2-fluorobenzyl N,N-di-sec-butyldithiocarbamate.

6. A method in accordance with claim 2 wherein X is O.

7. A method in accordance with claim 5 wherein said compound is 4-chlorobenzyl N,N-di-sec-butylthiolcarbamate.

8. A method in accordance with claim 5 wherein said compound is 4-fluorobenzyl N,N-di-sec-butylthiolcarbamate.

9. A method in accordance with claim 1 wherein said plants are soybean plants.

* * * * *